(12) United States Patent
Inoue

(10) Patent No.: US 6,210,386 B1
(45) Date of Patent: Apr. 3, 2001

(54) DISPOSABLE PULL-ON UNDERGARMENT WITH ROLL-UP ARRANGEMENT FOR ITS DISPOSAL

(75) Inventor: Yasushi Inoue, Kagawa-ken (JP)

(73) Assignee: Uni-Charm Corporation, Ehime-ken (JP)

(*) Notice: Subject to any disclaimer, the term of this patent is extended or adjusted under 35 U.S.C. 154(b) by 0 days.

(21) Appl. No.: 09/070,152

(22) Filed: Apr. 30, 1998

(30) Foreign Application Priority Data

Apr. 30, 1997 (JP) .................................................. 9-113211

(51) Int. Cl.⁷ ..................................................... A61F 13/72
(52) U.S. Cl. ............................. 604/385.13; 604/385.01; 604/385.03; 604/385.22; 604/385.24; 604/385.27; 604/385.29
(58) Field of Search ...................... 604/385.01, 385.03, 604/385.29, 385.3, 393, 394, 396

(56) References Cited

U.S. PATENT DOCUMENTS

| | | | |
|---|---|---|---|
| 4,034,760 | 7/1977 | Amirsakis | 128/287 |
| 4,923,455 * | 5/1990 | Dean et al. | 604/385.13 |
| 4,968,311 * | 11/1990 | Chickering et al. | 604/385.13 |
| 5,071,414 * | 12/1991 | Elliot | 604/385.13 |
| 5,141,505 | 8/1992 | Barrett | 604/385.1 |
| 5,290,268 | 3/1994 | Oliver et al. | 604/359 |
| 5,304,158 * | 4/1994 | Webb | 604/385.13 |

FOREIGN PATENT DOCUMENTS

| | | | |
|---|---|---|---|
| 49 6716 * | 7/1992 | (EP) | 604/FOR 103 |
| 0 684 029 A2 | 11/1995 | (EP) . | |
| 0 684 029 A3 | 11/1995 | (EP) . | |
| 2603170 * | 4/1988 | (FR) | 604/FOR 103 |
| 2 675 993 | 11/1992 | (FR) . | |
| 2675993 * | 11/1992 | (FR) | 604/FOR 103 |
| 5-21935 | 3/1993 | (JP) . | |
| 8-507699 | 8/1996 | (JP) . | |
| 88/06008 | 8/1988 | (WO) . | |
| 94/09736 | 5/1994 | (WO) . | |

* cited by examiner

Primary Examiner—John G. Weiss
Assistant Examiner—Michael Bogart
(74) Attorney, Agent, or Firm—Lowe Hauptman Gilman & Berner, LLP

(57) ABSTRACT

A disposable pull-on garment is provided along at least one of front and rear regions an auxiliary flap. The auxiliary flap is elastic circumferentially of the garment and has its circumferentially opposite side edges unitized with the waist region along transversely opposite side edges of this waist region.

11 Claims, 4 Drawing Sheets

FIG.3
FIG.4
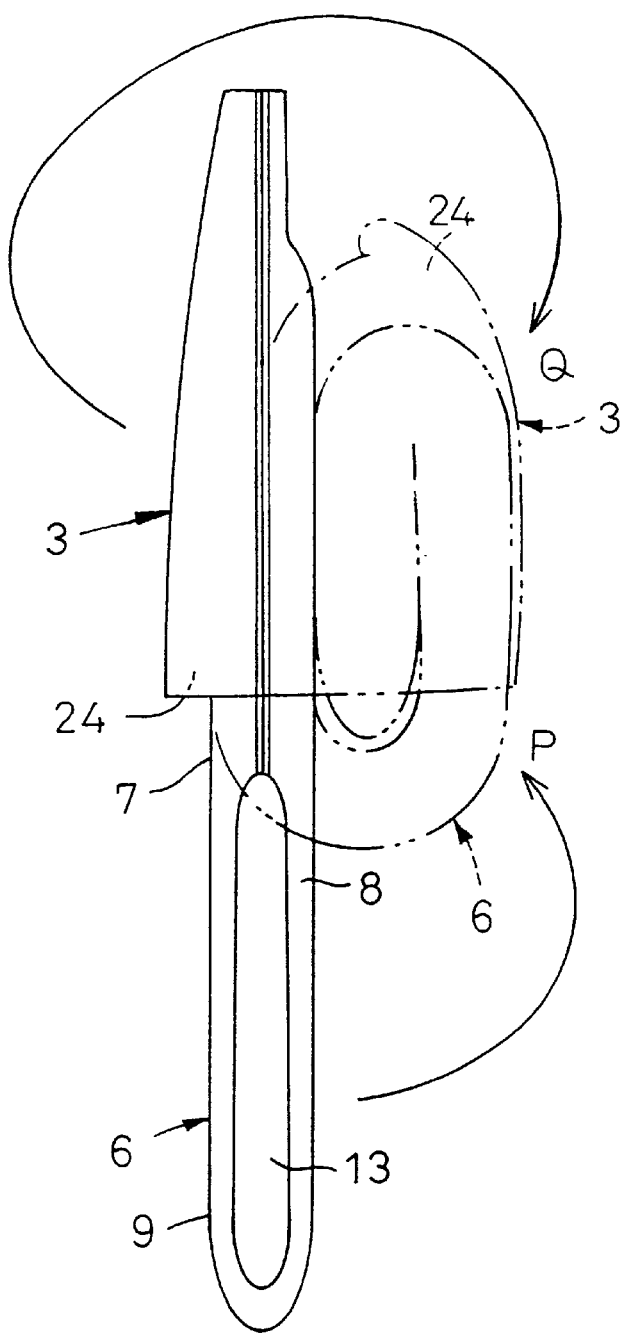
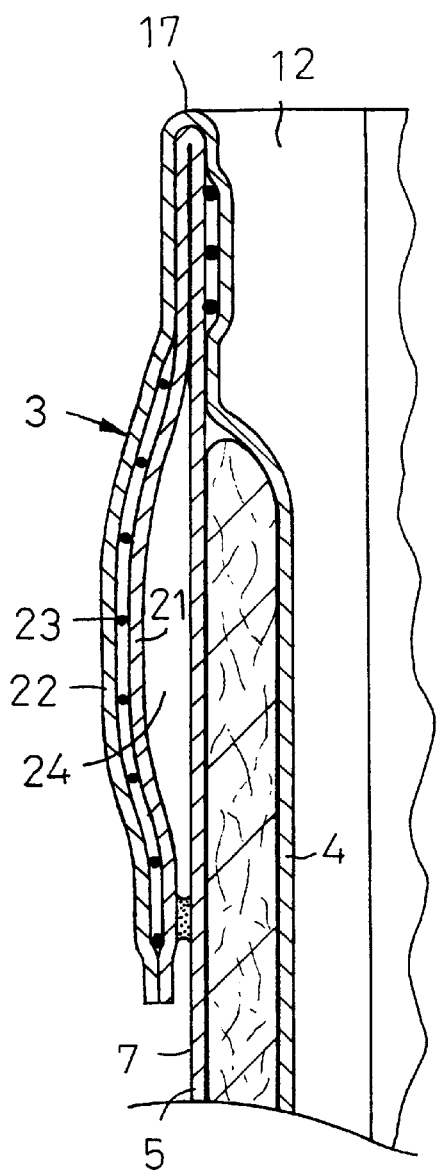

DISPOSABLE PULL-ON UNDERGARMENT WITH ROLL-UP ARRANGEMENT FOR ITS DISPOSAL

BACKGROUND OF THE INVENTION

This invention relates to a disposable pull-on garment and more particularly to a disposable pull-on garment including a pants type disposable diaper, training pants and incontinence pants, provided with structure functioning to improve fitting of the garment to a wearer's waist and to hold the garment in a rolled up state thereof for disposal.

Japanese Patent Application Toku Hyo (PCT) No. Hei8-507699 discloses a disposable pull-on diaper (Related Art 1) in which both front and rear waist regions are provided on their entire extent with a plurality of circumferentially contractile elastic members and the rear waist region is provided in its middle with a single adhesive strip being extendible vertically of the diaper. This arrangement enables fitting of the diaper to a wearer's waist and the used diaper to be rolled up for disposal using the adhesive strip.

Japanese Laid-Open Utility Model Application No. Hei5-21935 discloses a disposable pull-on diaper (Related Art 2) in which an adhesive sheet is separably fastened to an inner surface of the front or rear waist region of the diaper. This arrangement also enables the diaper to be rolled up for disposal using the adhesive sheet. The adhesive sheet has substantially the same width as the diaper and is adapted to be secured to the diaper which has been rolled from its bottom toward its top over the entire width of the diaper.

In the case of the foregoing Related Art 1, a relatively narrow single strip is used to hold the diaper in its rolled up state for disposal. This may cause leakage on offensive odor from the rolled up diaper because the waist-opening cannot be completely closed when the diaper is rolled up with the waist-opening being exposed.

In the case of the foregoing Related Art 2, the substantially entire waist-opening of the rolled up diaper can be closed by the adhesive sheet. However, any one of the front and rear waist regions remains covered with the adhesive sheet over the substantially entire width during use of the diaper and the adhesive sheet inevitably degrades the desired elasticity of this waist region in its circumferential direction.

According to both the foregoing Related Art 1 and the foregoing Related Art 2, the strip and the sheet used to hold the rolled up diaper are adhesive. If any extraneous matter clings to their adhesive surfaces during use of the diaper, the adhesive nature will seriously deteriorate and the strip as well as the sheet can be no longer be used to hold the rolled up diaper.

The elastic members and the strip employed by the foregoing Related Art 1 as well as the adhesive sheet employed by the foregoing Related Art 2 cannot offer two or more functions, respectively, so the number of members correspondingly increases manufacturing cost.

SUMMARY OF THE INVENTION

In view of the problem as has been described above, it is a principal object of the invention to provide a disposable pull-on garment provided with structure functioning not only to improve a fitting of the garment to a wearer's waist but also to hold the used garment in its rolled up state for disposal, wherein the structure is adapted, when it functions to dispose of the garment, to hold the used garment in its rolled up state without relying upon any adhesive fastener and preferably to cover the waist-opening of the rolled up garment over substantially entire extent of the opening.

The object set forth above is achieved, according to the invention, by a disposable pull-on garment having mutually opposite first and second waist regions and a crotch region therebetween comprising a liquid-permeable topsheet, a liquid-impermeable backsheet and a liquid-absorbent core disposed therebetween, said first and second waist regions being bonded together along transversely opposite side edges thereof, respectively, so as to form a waist-opening and a pair of leg-openings, wherein: an auxiliary flap extending in front of said backsheet in said first waist region and being elastic circumferentially of said garment has circumferentially opposite side edges thereof unitized with said first waist region along transversely opposite side edges of said first waist region.

The invention comprises the following various modes.

(1) The auxiliary flap comprises a nonwoven fabric and a plurality of elastic members circumferentially extending in parallel one to another and secured to said nonwoven fabric under appropriate tension.

(2) The auxiliary flap extends between a peripheral edge of said waist-opening and top edges of said leg-openings as viewed vertically of said garment.

(3) The auxiliary flap is unitized with said first waist region along said peripheral edge of said waist-opening and said transversely opposite side edges of said auxiliary flap, leaving a remaining portion spaced apart from said first waist region, so as to form a pocket opening downwardly of said garment.

(4) The auxiliary flap comprises a portion of at least one of said topsheet and backsheet extending outward beyond the peripheral edge of said waist-opening in said first waist region and folded downward along said peripheral edge.

(5) The auxiliary flap has transversely opposite side edges thereof unitized with said first waist-region so as to leave a remaining portion of said auxiliary flap spaced apart from said first waist region.

(6) The auxiliary flap defining said pocket is unitized with said first waist region along circumferentially opposite portions of a bottom edge of said flap defining said pocket opening therebetween so that said pocket opening has a width smaller than a width of an internal space of said pocket.

(7) The remaining portion of said auxiliary flap spaced from said first waist region has a dimension gradually reduced from the top edge toward the bottom edge of said garment.

(8) The remaining portion of said auxiliary flap spaced from said first waist region is separably fastened to said backsheet at intermittently distributed spots.

BRIEF DESCRIPTION OF THE DRAWINGS

FIG. 3 is a schematic side view of the diaper illustrating steps of procedure for rolling up the diaper after its used;

FIG. 4 is a view similar to FIG. 2 of an alternative arrangement;

DESCRIPTION OF THE PREFERRED EMBODIMENTS

Details of a disposable pull-on garment according to the invention will be more fully understood from the description of the pull-on diaper as a specific embodiment of the invention given hereunder with reference to the accompanying drawings.

Figure 2:
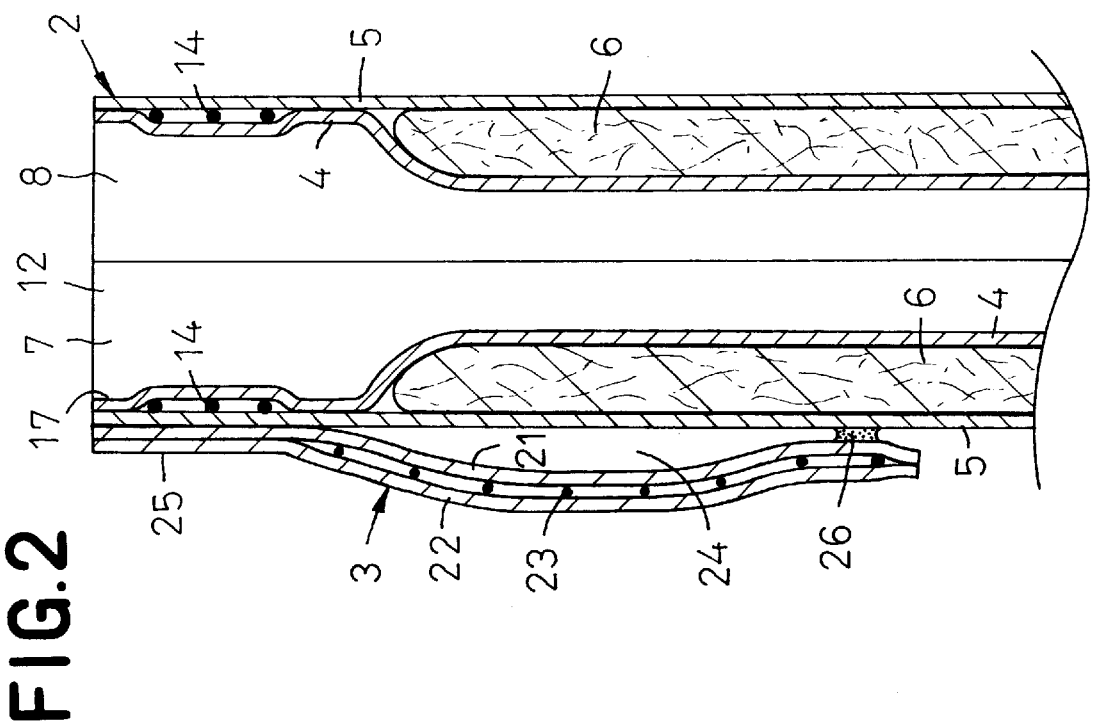
FIG. 2 is a sectional view taken along a line II—II in FIG. 1.
Figure 1:
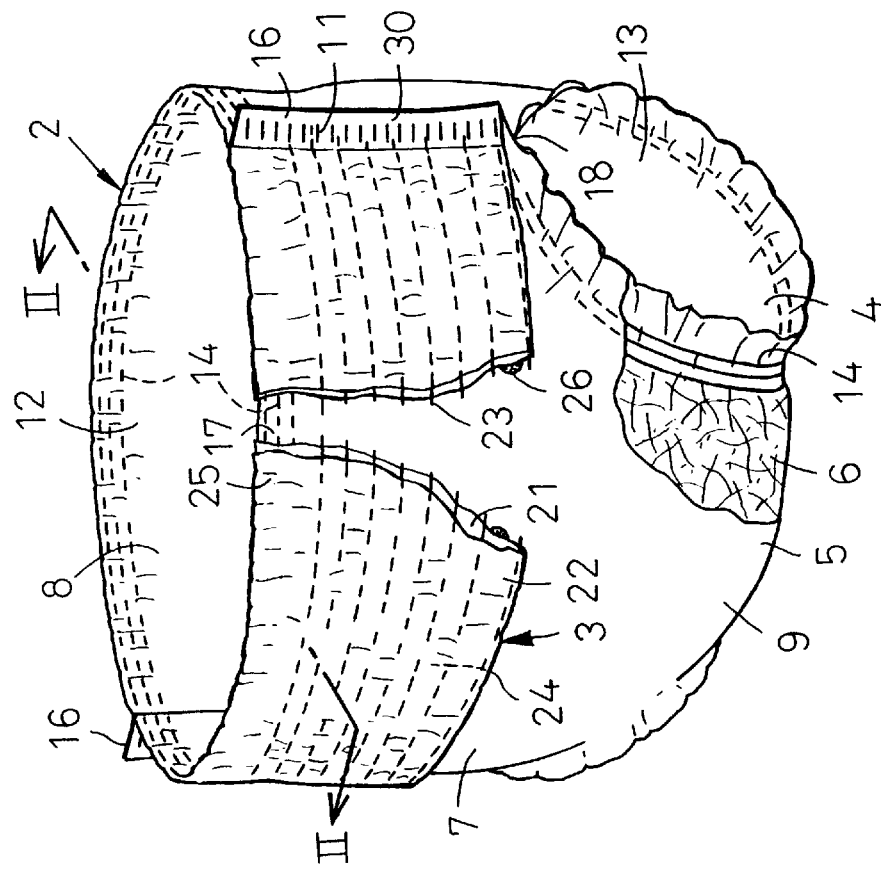
FIG. 1 is a perspective view of a disposable pull-on diaper as partially broken away.

FIGS. 1 and 2 are a perspective view of a disposable pull-on diaper as partially broken away and a sectional view taken along a line II—II in FIG. 1, respectively. The diaper includes a main body 2 of a pants type and an auxiliary flap 3 having stretchability and provided on an outer side of a front waist region 7 of the main body 2 as will be described later in more detail. The main body 2 comprises a liquid-permeable topsheet 4, a liquid-impermeable backsheet 5 and a liquid-absorbent core 6 disposed between these two sheets 4, 5. The main body 2 is defined by the front waist region 7, a rear waist region 8 and a crotch region 9. The topsheet 4 and the backsheet 5 extend outward beyond a peripheral edge of the absorbent core 6 and these extensions are bonded together by hot melt adhesive (not shown). The front and rear waist regions 7, 8 are put flat and bonded together at bonding spots arranged intermittently in their vertical directions along their transversely opposite side edges so as to form a pair of ears 16, a waist-opening 12 and a pair of leg-openings 13. Along peripheral edges of the respective openings 12, 13, elastic members 14 extend circumferentially of these openings 12, 13. These elastic members 14 are disposed between the topsheet 4 and the backsheet 5 and bonded to an inner surface of at least one of these two sheets under appropriate tensions, respectively.

One purpose of the auxiliary flap (or flaps) 3 is to maintain the front and rear waist regions 7, 8, particularly the front waist region 7, elastically in close contact with a wearer's body, on one hand, and to hold the diaper in its rolled up state after use, on the other hand. In the case of a single auxiliary flap 3 used in association with the front waist region 7, the flap 3 covers substantially the entire front waist region 7 by extending transversely between the pair of ears 16 and vertically between a peripheral edge 17 of the waist-opening 12 and top edges 18 of the respective leg-openings 13. The auxiliary flap 3 comprises an inner sheet member 21, an outer sheet member 22 and a plurality of elastic members 23 disposed between these two sheet members 21, 22. The inner and outer sheet members 21, 22 have their inner surfaces bonded together by hot melt adhesive (not shown). The elastic members 23 extend parallel to one another circumferentially of the diaper and are secured to an inner surface of at least one of the inner and outer sheet members 21, 22 under appropriate tension.

The auxiliary flap 3 constructed as described above is connected to the main body 2 at its circumferentially opposite side edges 30 which are bonded to the respective ears 16 of the main body 2 at the bonding spots 11. Additionally, the auxiliary flap 3 is also connected along its top edge 25 to the peripheral edge 17 of the main body 2 and cooperates with the front waist region 7 to define a pocket 24 opening downward. It should be understood that an inner surface of the inner sheet member 21 is separably fastened to an outer surface of a backsheet 5 by means of glue 26 intermittently applied on the inner surface of the inner sheet member 21 in order to maintain the pocket 24 closed during use of the diaper. In this manner, the front and rear waist regions 7, 8, particularly the front waist region 7 can be elastically maintained in close contact with the wearer's body during use of the diaper under the contractile effect of the elastic members 23 provided in the auxiliary flap (or flaps) 3.

FIG. 3 is a schematic side view of the diaper illustrating the steps of procedure for rolling up the diaper after its use. After the diaper has been used, the main body 2 of the diaper is flattened with the front and rear waist regions 7, 8 placed one upon another, then starting from the bottom, i.e., the crotch region 9, the main body 2 is rolled upward with the rear waist region 8 laid inside as indicated by an arrow P. Then, the auxiliary flap 3 is folded back toward the rear waist region 8 so as to turn the pocket 24 inside out as indicated by an arrow Q and the main body 2 thus rolled up is received into the pocket 24 thus turned inside out. Elasticity of the auxiliary flap 3 facilitates not only the pocket 3 being turned inside out but also insertion of the main body 2 being received into the pocket 3. The main body 2 is effectively held in its rolled up state under the contractile effect of the auxiliary flap 3. Disposal of the used diaper may be done in this state without any apprehension that undesirable leakage of offensive odor as well as excretion might occur through the waist-opening 12 and the leg-openings 13 because both the waist-opening 12 and the leg-openings 13 are reliably confined in the pocket 24 and never exposed.

In the diaper constructed as has been described hereinabove, the inner and outer sheet members 21, 22 of the auxiliary flap 3 may be formed by a nonwoven or woven fabric or a plastic film, more preferably, a breathable nonwoven or a woven fabric or a plastic film. While the inner sheet member 21 and the outer sheet member 22 may be formed by the same sheet material, it is also possible to obtain these sheet materials 21, 22 by combining two types of material which are different from each other in appearance and basis weight. The topsheet 4 may be formed by a liquid-permeable nonwoven fabric, a porous plastic film or the like. The backsheet 5 may be formed by liquid-impermeable, more preferably, not only a liquid-impermeable but also breathable plastic film or the like. The liquid-absorbent core 6 may be formed by fluff pulp, a mixture of such fluff pulp and water absorptive polymer, or the like. Bonding of various components of the diaper may be carried out by, in addition to use of any suitable adhesive agent such as a hot melt adhesive agent, using the heat-sealing technique so far as the components to be bonded together are of thermoplastic nature. For example, the inner and outer sheet members 21, 22 of the auxiliary flap 3 may be formed by a nonwoven fabric made of thermoplastic synthetic fiber and these two sheet members 21, 22 may be intermittently heat-sealed with each other.

FIG. 4 is a view similar to FIG. 2 showing an alternative embodiment of the invention. In this specific embodiment of the diaper, the portions of the topsheet 4 and the backsheet 5 defining together the front waist region 7 extend beyond and folded along the peripheral edge 17 of the waist-opening 12 downwardly of the diaper so that these extensions may form the auxiliary flap 3. These extensions of the topsheet 4 and the backsheet 5 respectively define the outer sheet member 22 and the inner sheet member 21. Between these inner and outer sheet members 21, 22, a plurality of elastic members 23 is disposed to extend transversely of the auxiliary flap 3 and bonded under appropriate tension to one of the two sheet members 21, 22 as in the case of FIG. 2. The sheet members 21, 22 are intermittently bonded to each other by means of hot melt adhesive (not shown). The sheet members 21, 22 have their transversely opposite side edges 30 bonded to the respective ears 16 of the main body 2.

According to this alternative embodiment, the auxiliary flap 3 may be formed by the topsheet 4 or the backsheet 5 alone. It is also possible to bond a third sheet member to the extension of the topsheet 4 and/or the backsheet 5 which has been folded downward and thereby to form the auxiliary flap 3.

Figure 5:
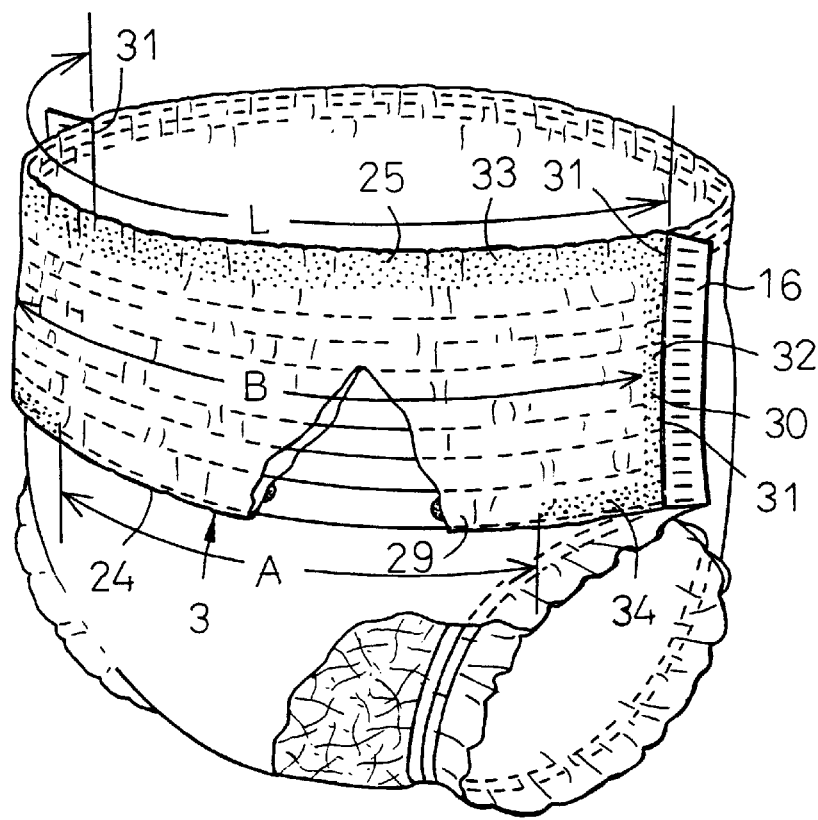
FIG. 5 is a view similar to FIG. 1 of an alternative embodiment.

FIG. 5 is a view similar to FIG. 1 showing another embodiment of the invention. According to this specific embodiment, the auxiliary flap 3 extends between respective proximal ends 31 of the ears 16 provided along transversely opposite side edges of the basic structure 2 over a length L. The auxiliary flap 3 has circumferentially opposite side edges 30, top edge 25 and a part of bottom edge 29 respectively bonded by means of hot melt adhesive (not shown) to an outer surface of the backsheet 5 in the front waist region 7 on areas 32, 33, 34 indicated by a large number of dots. With this diaper, an opening of the pocket 24 defined by the auxiliary flap 3 has a width A smaller than a width B of an internal space defined by this pocket 24. Consequently, once the main body 2 has been put into the pocket 24 turned inside out as shown by FIG. 3, there is no possibility that the main body 2 might readily bulge out of the pocket 24. In order to avoid any apprehension that the side edges 30 of the auxiliary flap 3 might be unintentionally peeled off from the main body 2 as the diaper is torn along the ears 16 into the front and rear waist regions 7, 8 take the diaper off from the wearer's body and the auxiliary flap 3 could not function as the pocket, the transversely opposite side edges may be bonded to the front waist region 7 in the vicinity of the respective proximal ends 31 of the ears 16 rather than to the ears 16 of the main body 2. It should be understood here that, so long as the opening of the pocket 24 is arranged as shown in FIG. 5, the side edges 30 may be bonded to the ears 16 themselves as shown in FIG. 1 or may be bonded not only to the ears 16 but also to the front waist region 7 in the vicinity of their proximal ends 31.

Figure 6:
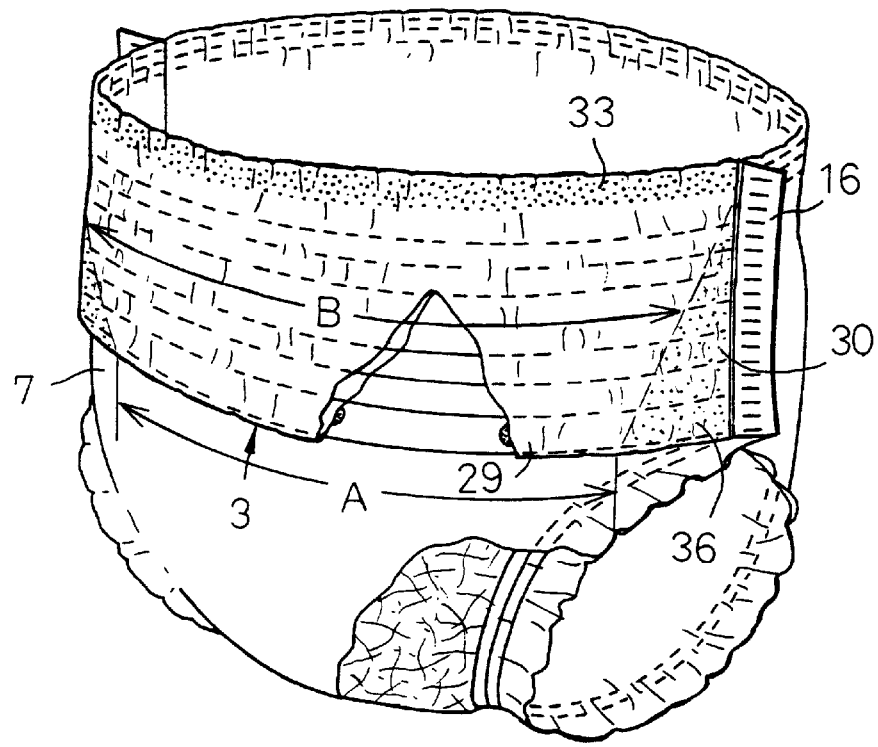
FIG. 6 is a view similar to FIG. 1 of still another embodiment.

FIG. 6 is a view similar to FIG. 5 showing still another embodiment of the invention. While the auxiliary flaps in this embodiment has a configuration similar to that in the previous embodiment shown by FIG. 5, the auxiliary flap 3 in this embodiment is bonded along its side edges 30 and bottom edge 29 to the front waist region 7 on an area 36 indicated by a large number of dots. In this embodiment also, the opening of the pocket 24 has a width A smaller than a width B of an internal space defined by the pocket 24 and therefore the same effect as the diaper of FIG. 5 offers can be obtained.

Figure 7:
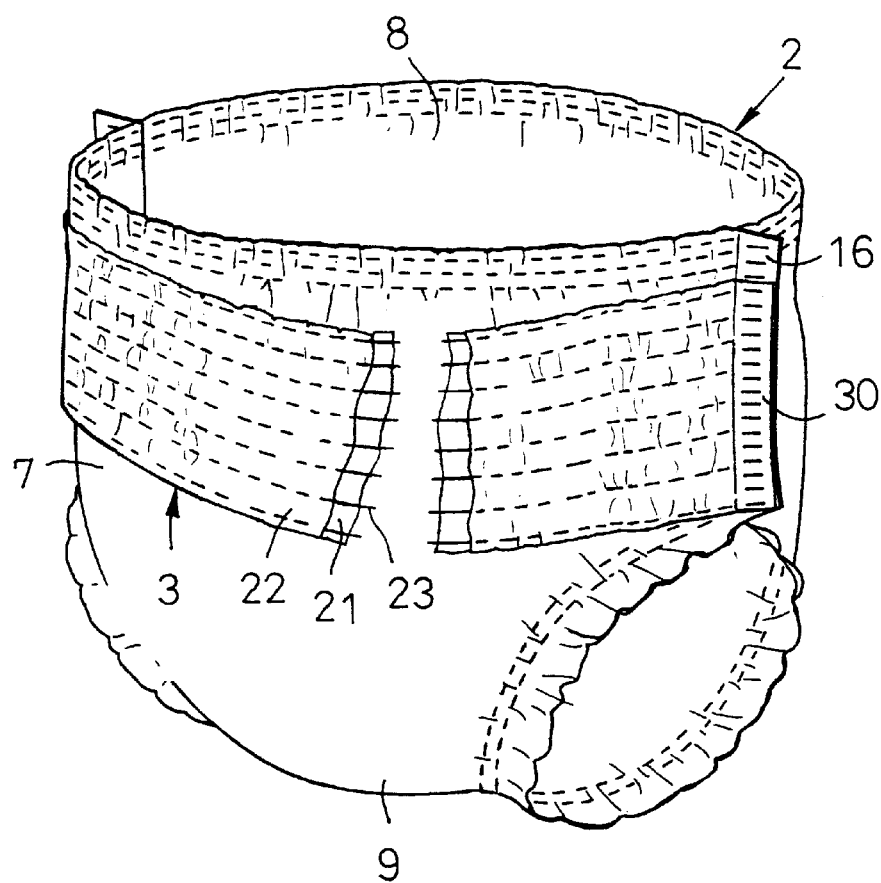
FIG. 7 is a view similar to FIG. 1 of a further another embodiment.

FIG. 7 is a perspective view showing further another embodiment of the invention as partially broken away. According to this embodiment, the auxiliary flap 3 is a belt-like flap circumferentially extending over the front waist region 7 and is bonded at its circumferentially opposite side edges 30 to the ears 16 of the main body 2, leaving its intermediate portion spaced from the front waist region 7. The auxiliary flap 3 comprises, similarly to that shown by FIG. 1, the inner and outer sheet members 21, 22 and the elastic members 23 making the flap 3 circumferentially elastic.

Figure 8:
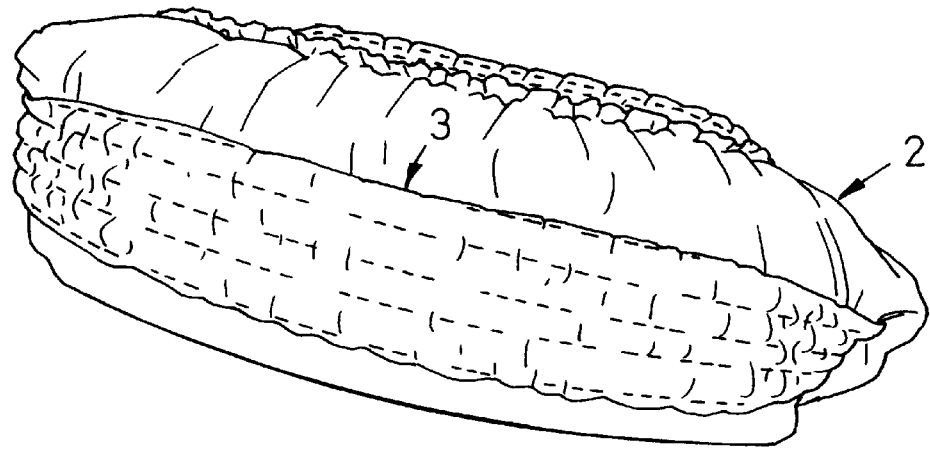
FIG. 8 is a perspective view of the diaper rolled up after use.

FIG. 8 is a perspective view showing the diaper held in its rolled up state using the auxiliary flap 3 according to the embodiment shown by FIG. 7. Starting from the bottom, i.e., the crotch region 9 of the diaper, the diaper is rolled up with the rear waist region 8 laid inside, then the auxiliary flap 3 folded back onto the rear waist region 8 so as to be turned inside out, just as in the case of the pocket 24, and thereby to cover the main body 2. In this embodiment, no pocket is formed by the auxiliary flap 3 and, as a result, it is difficult to completely cover the waist-opening 12 as well as the leg-openings 13. However, no sticky material is used by this embodiment to hold the main body 2 in its rolled up state and therefore there is no possibility that any extraneous matter sticking to this material might prevent the main body 2 from being held in its rolled up state.

While the invention has been described above with respect to the disposable diaper of pants type as a specific embodiment, the invention can be implemented also in the form of the other disposable garments of pants type such as training pants and incontinence pants.

The auxiliary flap 3 may be provided in association with the rear waist region 8, instead of with the front waist region 7 or in association with both the front waist region and the rear waist regions.

With the disposable garment of pants type according to the invention, the auxiliary flap elastically biases the associated waist region in close contact with the wearer's waist under the contractile effect of the auxiliary flap for an improved fitness during use of the garment. After use of the garment, the auxiliary flap stretchably extending between the transversely opposite side edges of the associated waist region can be effectively used to hold the used garment in its rolled up state. The auxiliary flap-according to the invention employs none of sticky means and therefore there is no possibility that any extraneous matter clinging to such sticky means might make such sticky means ineffective and make it impossible to roll up the used garment as the well known garment of this type has often been the case.

With the garment in which the auxiliary flap forms the pocket, merely by rolling up the garment after its use and putting it into the pocket, undesirable leakage of offensive odor and/or excretion through the waist-opening and/or the leg-openings can be avoided.

The disposable garment according to the invention is less expensive than the conventional garment of this type in which the front or rear waist region is provided with both the auxiliary elastic means and the means for disposal of the used garment such as tape fastener because the auxiliary flap of the invention offers two functions as has been described above.

What is claimed is:

1. A disposable pull-on undergarment comprising:
   a liquid-permeable topsheet;
   a liquid-permeable backsheet;
   a liquid-absorbent core disposed between said topsheet and said backsheet;
   said topsheet, backsheet and core defining first and second waist regions and a crotch region extending between said first and second waist regions;
   said first and second waist regions being bonded together along transversely opposite side edges thereof, respectively, so as to form a waist-opening and a pair of leg-openings; and
   an auxiliary flap extending in front of said backsheet between said transversely opposite side edges of said first region, wherein said auxiliary flap comprises a nonwoven fabric and a plurality of elastic members extending circumferentially of said waist opening and secured to said nonwoven fabric under tension.

2. The garment according to claim 1 wherein said auxiliary flap extends between a peripheral edge of said waist-opening and top edges of said leg-openings as viewed vertically of said garment.

3. The garment according to claim 1, wherein said auxiliary flap is unitized with said first waist region along a peripheral edge of said waist-opening and said transversely opposite side edges of said auxiliary flap, leaving a remaining portion spaced from said first waist region, so as to form a pocket opening downwardly of said garment.

4. The garment according to claim 3, wherein said auxiliary flap comprises a portion of at least one of said topsheet and said backsheet extending outward beyond the peripheral edge of said waist-opening in said first waist region and folded downward along said peripheral edge.

5. The garment according to claim 1, wherein said auxiliary flap has transversely opposite side edges thereof unitized with said first waist region so as to leave a remaining portion of said auxiliary flap spaced apart from said first waist region.

6. The garment according to claim 3, wherein said auxiliary flap defining said pocket is unitized with said first waist region along circumferentially opposite portions of a bottom edge of said flap defining said pocket opening therebetween so that said pocket opening has a width smaller than a width of an internal space of said pocket.

7. The garment according to claim 3, wherein said remaining portion of said auxiliary flap spaced from said first waist region has a dimension gradually reduced from the top edge toward the bottom edge of said auxiliary flap.

8. The garment according to claim 3, wherein said remaining portion of said auxiliary flap spaced from said first waist region is separably fastened to said backsheet at intermittently distributed spots.

9. A disposable pull-on undergarment, comprising:

a liquid-permeable topsheet;

a liquid-impermeable backsheet;

a liquid-absorbent core disposed between said topsheet and said backsheet;

said topsheet, backsheet and core defining first and second waist regions and a crotch region extending between said first and second waist regions;

said first and second waist regions being bonded together along transversely opposite side edges thereof, respectively, so as to form a waist-opening and a pair of leg-openings; and an auxiliary flap extending in front of said backsheet between said transversely opposite side edges of said first region wherein said auxiliary flap comprises elastic extending circumferentially of said waist opening, wherein said auxiliary flap defining said pocket is unitized with said first waist region along circumferentially opposite portions of a bottom edge of said flap defining said pocket opening therebetween so that said pocket opening has a width smaller than a width of an internal space of said pocket.

10. A disposable pull-on undergarment, comprising:

a liquid-permeable topsheet;

a liquid-impermeable backsheet;

a liquid-absorbent core disposed between said topsheet and said backsheet;

said topsheet, backsheet and core defining first and second waist regions and a crotch region extending between said first and second waist regions;

said first and second waist regions being bonded together along transversely opposite side edges thereof, respectively, so as to form a waist-opening and a pair of leg-openings; and an auxiliary flap extending in front of said backsheet between said transversely opposite side edges of said first region wherein said auxiliary flap comprises elastic extending circumferentially of said waist opening, said auxiliary flap is unitized with said first waist region along said peripheral edge of said waist-opening and said transversely opposite side edges of said auxiliary flap, leaving a remaining portion spaced from said first waist region, so as to form a pocket opening downwardly of said garment, wherein said remaining portion of said auxiliary flap spaced from said first waist region has a dimension gradually reduced from the top edge toward the bottom edge of said auxiliary flap.

11. A disposable pull-on undergarment, comprising:

a liquid-permeable topsheet;

a liquid-impermeable backsheet;

a liquid-absorbent core disposed between said topsheet and said backsheet;

said topsheet, backsheet and core defining first and second waist regions and a crotch region extending between said first and second waist regions;

said first and second waist regions being bonded together along transversely opposite side edges thereof, respectively, so as to form a waist-opening and a pair of leg-openings; and an auxiliary flap extending in front of said backsheet between said transversely opposite side edges of said first region wherein said auxiliary flap comprises elastic extending circumferentially of said waist opening, said auxiliary flap is unitized with said first waist region along said peripheral edge of said waist-opening and said transversely opposite side edges of said auxiliary flap, leaving a remaining portion spaced from said first waist region, so as to form a pocket opening downwardly of said garment, and said remaining portion of said auxiliary flap spaced from said first waist region is separably fastened to said backsheet at intermittently distributed spots.

* * * * *